United States Patent [19]

Leysieffer et al.

[11] Patent Number: 4,791,620
[45] Date of Patent: Dec. 13, 1988

[54] TACTILE HEARING AID

[75] Inventors: Hans Leysieffer, Taufkirchen; Eberhard Zwicker, Icking, both of Fed. Rep. of Germany

[73] Assignee: Siemens Aktiengesellschaft, Berlin and Munich, Fed. Rep. of Germany

[21] Appl. No.: 842,822

[22] Filed: Mar. 21, 1986

[30] Foreign Application Priority Data

Mar. 22, 1985 [DE] Fed. Rep. of Germany ....... 3510508

[51] Int. Cl.⁴ .................. H04B 1/06; H04R 25/00
[52] U.S. Cl. .................................... 367/135; 381/68.2; 367/116
[58] Field of Search ............... 367/110, 116, 135; 381/68, 68.2, 151, 190; 310/800; 342/25; 128/1.6

[56] References Cited

U.S. PATENT DOCUMENTS

| | | | |
|---|---|---|---|
| 4,109,116 | 8/1978 | Victoreen | 381/68 |
| 4,139,742 | 2/1979 | Walker | 381/68 |
| 4,150,262 | 4/1979 | Ono | 381/68.3 |
| 4,403,382 | 9/1983 | Facoetti et al. | 310/800 |
| 4,581,491 | 4/1986 | Boothroyd | 381/68 |
| 4,628,907 | 12/1986 | Epley | 381/68.3 |

FOREIGN PATENT DOCUMENTS 1231085 9/1960 France .
56-47199 4/1981 Japan .

OTHER PUBLICATIONS

"Fortschritte der Akustik", Sessler, pp. 81–99.
"Piezoelectricity in Polyvinylindenefluoride", Sessler, J. Acoust. Soc. Am. 70(6), Dec. 1981, pp. 1596–1608.
"Uses of Computers in Aiding the Disabled", Ifukuba, Proceedings of the IFIP-IMIA Working Conference on Uses of Computers in Aiding the Disabled, Nov. 3–5, 1981 pp. 157–215.

Primary Examiner—Thomas H. Tarcza
Assistant Examiner—Daniel T. Piholic

[57] ABSTRACT

A tactile hearing aid has electro-mechanical transducers which emit vibrations to the sense of touch of the skin surface for the transmission of signals. The transducers are small and lightweight and have low power consumption. The vibratory member is composed of piezoelectric, high-polymer material and has the form of a film which is provided with electically conductive coatings at both sides between which the signals to be transmitted can be applied. The film may be bent to form a ring and may be arranged in a folded stack of a number of plies to the outside surface of a carrier ring which is approximately 90° open. The transducer can thus be worn on the fingers of a hand. The transducer unit is employable with particular advantage in devices for the transmission of messages via the sense of touch such as in hearing prothesis for persons extremely hard of hearing or for deaf persons.

23 Claims, 8 Drawing Sheets

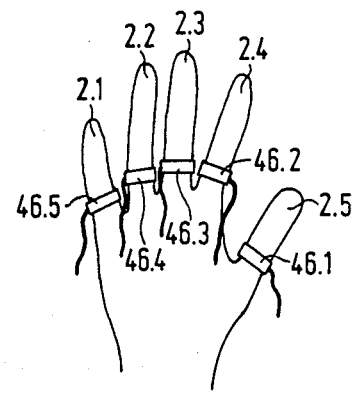
FIG 12
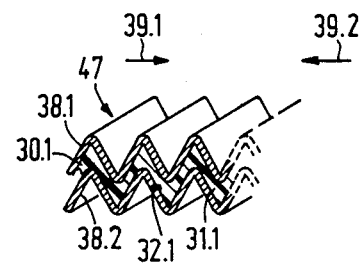
FIG 13
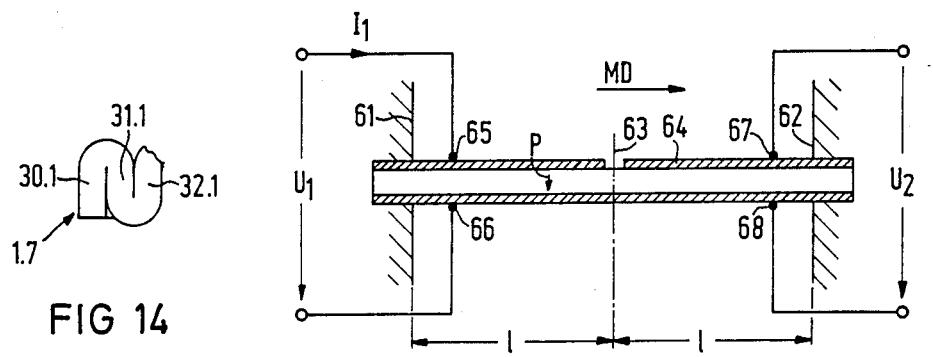
FIG 14
FIG 15
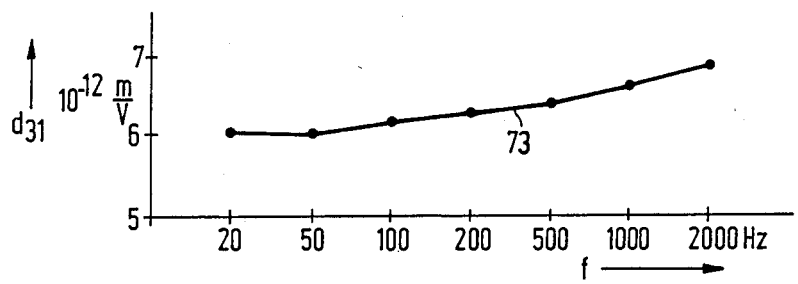
FIG 16

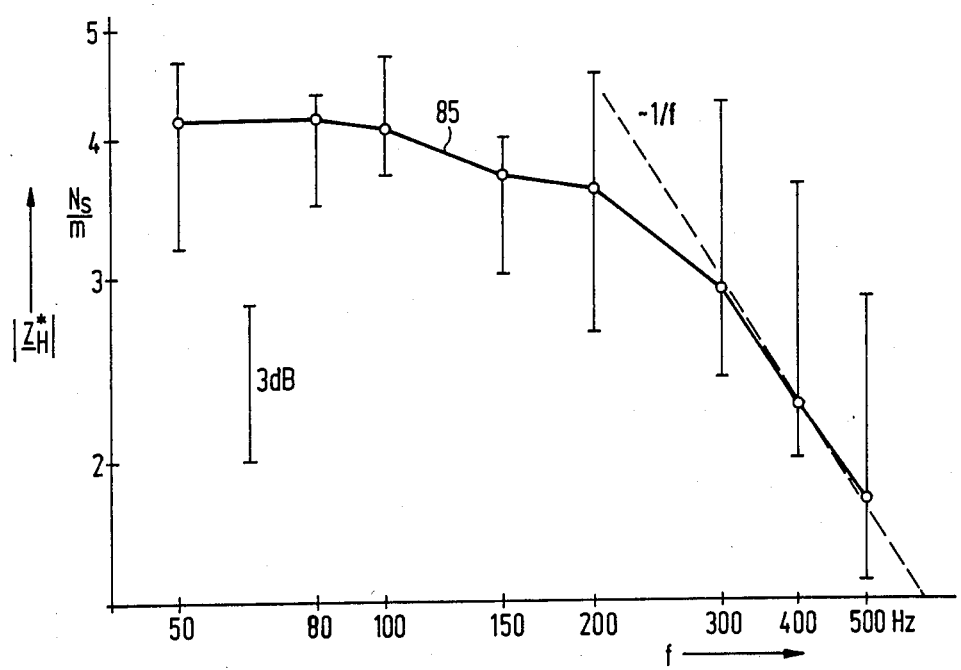
FIG 22
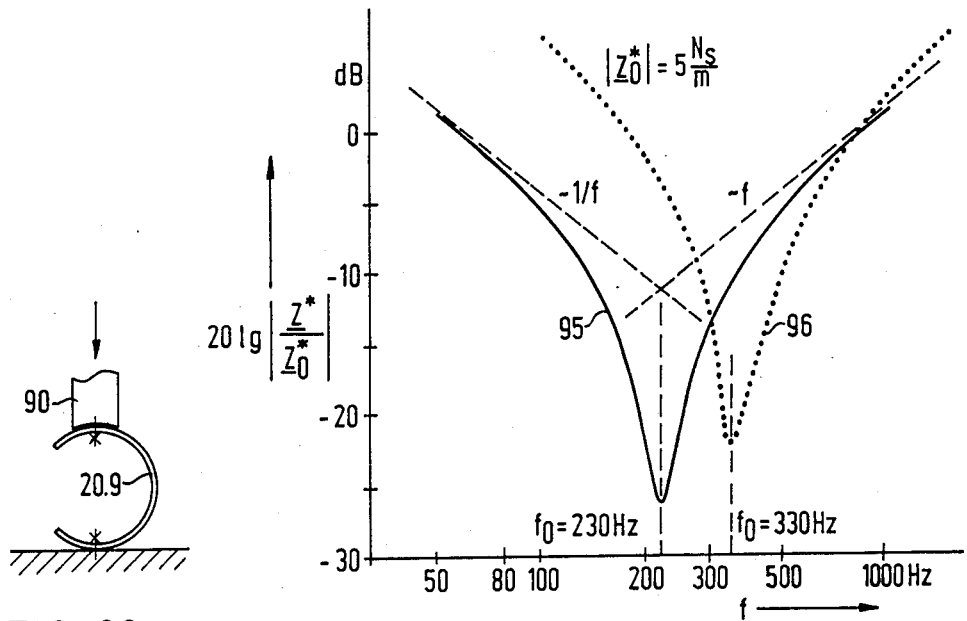
FIG 23
FIG 24

TACTILE HEARING AID

BACKGROUND OF THE INVENTION

1. Field of the Invention

The invention relates to tactile devices for producing a signal preceivable as an audio signal, which may be used as a hearing aid.

2. Description of the Prior Art

Tactile hearing aids are known, for example in U.S. Pat. No. 4,139,742, wherein communications, principally acoustical information such as speech, are converted into electrical signals which are then transmitted by mechanical stimulation to the surface of the skin, i.e., to the sense of touch. Messages can still be conveyed with this hearing aid even when they could not be perceived by normal bearing because of a loud and unsurveyable environment because of a hearing deficiency or when an acoustical perception is impossible because of deafness. Like standard hearing aids, these systems should also be an unobtrusive as possible and should be capable of being used without significant negative effect on the activities of daily life. What is required for this purpose is an arrangement which is light and small and which operates with a low power consumption so that it can be operated with portable current sources such as batteries. Only in this fashion is a device independent of the mains and of the type which can be unobtrusively carried. The power consumption should be able to be maintained at least for the duration of ten hours by means of mobile current sources such as batteries without an interruption being required.

It has proven beneficial, particularly in hearing aids for extremely pronounced reductions in the hearing faculty, to make use of tactile transmission. In comparison to electrocutaneous system, improved chronological resolution of the sense of touch and better time invariancy of the threshold of sensation are achieved among other things. Heretofore, however, suitable electro-mechanical transducers have been lacking. Particularly in multi-channel devices and vocoder systems, for instance those known from French Pat. No. 12 31 085, conventional electro-mechanical transducers cannot be used because they are too heavy and too large. The demands for low volume and low weight cannot be met with the standard electromagnets due to the physical principle employed.

Even piezoceramic transducers employed in more recent systems known, for instance, from the publication by T. Ifukube, "A Cued Tactual Vocoder" in JFGP-JMJA Working Conference on Uses of Computers in Aiding the Disabled, Haifa, 1981, containing flexural resonators working according to the bimorph principle have not gained acceptance. The piezoceramic provided for the manufacture of these resonators is extremely sensitive in mechanical terms. It must therefore be adequately protected, whereby the necessary volume must be increased beyond an acceptable degree.

Numerous investigations have shown that the hand is best suited for the transmission of audio signals via multi-channel systems upon employment of vibrations. The breakable ceramic elements, however, are exposed to particularly severe mechanical demands when worn on the hand.

SUMMARY OF THE INVENTION

An object of the invention is to provide a tactile hearing aid wherein piezoelectrical transducers are provided which resist stresses occurring while worn on the hand and which have small volume and low weight given adequate effectiveness.

A lightweight and small embodiment of a transmitter in a tactile hearing aid is achieved by the employment of piezoelectric, high-polymer substances for constructing this element, these substances being described, for instance, in "Fortschritte der Akustik", DAGA 1976 (VDE Verlag, Berlin 1976), pages 81 through 95. Moreover, these substances, such as, for instance, polyvinylchloride (PVC) or polyvinylidenefluoride (PVDF) are very insensitive in mechanical terms. This is particularly apparent given polyvinylidenefluoride (PVDF), the following properties having proven beneficial for the employment thereof under the conditions of the invention:

(a) Small Dimensions:

Electro-dynamic systems which are commercially available vary from 8 through 30 $cm^3$ in overall volume. They are therefore not particularly suitable, especially for multi-channel vibrator arrays, since it is not possible to wear them unobtrusively under clothing. The PVDF transducers are extremely adaptable in dimensions (width and radius of a ring) and can be well adapted to a variety of prescriptions, for example devices for adults or for children.

Experiments for protecting the transducers by cladding them with a mechanically and chemically covering substance such as silicone rubber have shown that thin layers already offer adequate protection. The overall thickness can be limited to 1.5 mm and the maximum volume of the transducers can thus be kept below 1 $cm^3$. It is thus even smaller than that of piezoceramic transducer systems.

(b) Low Weight:

Favorable properties are achieved with PVDF transducers whose full weight lies below 2 g. Transducers of the invention are therefore well-suited for employment as stimulators in hearing aids for children. The required limitation to a maximum mass of about 15 through 20 g is far from being reached with the arrangement of the invention. Multi-channel systems are therefore unobjectionable from the point of view of the weight load on the user.

(c) High Efficiency:

High power consumption of standard electro-mechanical stimulators makes their application in standard hearing aids problematical because the required current sources become too heavy. Operation with batteries should be possible over a plurality of hours, for instance 10 hours. The high volume and weight of even the most modern accumulators produce an arrangement which possesses too little mobility for a user.

Although the efficiency of the PVDF transducers of the invention lies below 0.1%, the power consumption at the threshold of sensation only amounts to about 0.1 mW as a result of the selection of a highly sensitive place of stimulation. Given an excitation 20 dB above the threshold of sensation, power consumption reaches 10 mW; this values lies on the same order of magnitude as that which has been identified in optimized, electrocutaneous devices given the same intensity of sensation (approximately 6 mW). Tests with an electro-dynamic vibrator of the system "Fonotor" have shown that this commercially employed stimulator lies roughly 15 dB above the described PVDF transducers. A piezoceramic resonant transducer for operation in the underarm region consumes 1.25 mW at the threshold and is thus 11 dB poorer than the PVDF stimulators. The inherently low efficiency of the PVDF elements therefore plays a subordinate part.

(d) Favorable Dynamic Systems Behavior in the Frequency Range:

This demand is highly dependent on the design of the transmission system. Because the curves of identical degree of sensation approximately proceed from the curve of the threshold of sensation by parallel shift, corresponding distortion-correction networks into which the frequency response of the transducers can be co-incorporated must be provided given frequency-modulated systems. Since the strength of sensation in the sense of touch as well as in hearing is formed from the intensity of the physical stimulation via an exponential law and, given mechanical excitation, this is proportional to the square of velocity, frequency resonance corrections must likewise be undertaken given, for example, linear imaging of the curve onto the level of sensation. Under skin load, the PVDF transducers exhibit a monotone frequency response to the curve without resonances and can therefore be adapted to the required transmission goal (rhythm, pitch, etc.) with low circuit-technical outlay. In broad band transmission systems, however, the volume range available is limited by the band-pass characteristic of the threshold of sensation and of the curves of identical levels of sensation when a frequency-independent maximum transducer operation voltage is assumed.

(e) Suppression of the Sound Emission of the Transducer:

In order to keep from disturbing the environment of the user of a tactile hearing aid, it is undesirable for stimulators to emit sound in the audible frequency and volume range. This phenomenon which is problematical in electro-dynamic vibrator arrays was not observed in any operating condition of the PVDF transducers constructed in accord with the invention.

(f) Insensitivity to Static Bearing Pressure:

For contacting, the transducers lie on the surface of the skin under slight mechanical stress. A deterioration of the effect cannot, however, thereby be registered. A reduction in the volume range likewise did not occur when the bias voltage was additionally increased.

(g) Low Distortion:

Due to the band-pass characteristic of the curves of identical levels of sensation, this demand likewise plays an insignificant part. Given systems which predominately operate in the low-frequency range $30 \text{ Hz} \leq f \leq 100 \text{ Hz}$, however, preceptible distortion products can occur at high non-linear distortion factors of the transducers. In PVDF transducers, all high harmonics lie noticeably below the threshold of sensation due to the high harmonic distortion attentuation ($>50$ dB at maximum level).

(h) Great Volume Range:

Preliminary tests with a silicon rubber cladding of the transducers show that the available range of volume is thereby presumably reduced by only 6 through 8 dB. In methods which transmit speech information via an amplitude modulation of a sinusoidal 200 Hz carriers, therefore, only slight compression factors of the envelope volume of the voice signal are required.

(i) Low Long-Term Burden on the User:

The employment of any prothesis is determined to a not inconsiderable degree by psychological and cosmetic points of view. Even a PVDF transducer may still be found budensome that the freedom of mobility of the hand is limited given employment of a multi-channel system on a hand. Given one-channel transmission, however, this would hardly be of significance since the transducer can be unobtrusively worn like a finger ring. The low power consumption and pleasing structure of the PVDF stimulators reduce a bulky and heavy processing system to a small, easily wearable device which can be operated for many hours. It is to be anticipated that a system equipped with these transducers will be accepted and employed by more deaf persons than the large and heavy devices presently available.

(j) Operating Reliability:

Long-term tests have shown that PVDF is extremely stable given the conditions of employment in vibration transducers. Its properties change minimally or do not change at all over the course of time as long as great temperature fluctuations are avoided (below 25° and above +80° C.). Silicone rubber can be a suitable cladding material which keeps acids of skin perspiration away from the film metallization. Polyvinylidene fluoride resists many acids and caustic solutions. Other essentially negative influences on PDVF given employment in transducers of tactile hearing protheses are not currently known.

Tests have shown that commercially available PVDF is suitable for electro-mechanical transducers for stimulation at the finger members of the human hand. The impediment that the freedom of mobility of a hand is lessened due to the employment of such transducers is noticeably alleviated by the significant advantage of the smaller volume and weight as well as of the low power consumption of the stimulators. The employment of the transducers in multi-channel systems is thus also conceivable in the case of deaf infants who can in no case be burdened by heavy and bulky devices in addition to their impediment. The threshold of sensation tests which showed that the vibratory sensation of the new transmitters remains locally limited to the respectively excited finger member also indicate that the employment of these transducers is also advantageous in, for instance, the multi-channel vibrator systems known from French Pat. No. 12 31 085. On the hand, the PVDF stimulators are also highly suited for supplying the essential additional information during lip reading given single-channel methods for the transmission of the fundamental voice frequency and simple features such as sentence stress and rhythm.

DESCRIPTION OF THE DRAWINGS

FIG. 12 shows the arrangement of one or more transducers on a hand.

FIGS. 13 and 14 show a modified structure of a multi-ply folded stack.

FIG. 15 shows an arrangement for identification of the long-term stability of the PVDF constant $D_{31}$.

FIG. 16 shows the frequency dependency of the constant $D_{31}$ ($\hat{U}_1$=20 V).

FIG. 22 shows the mechanical skin impedance/$\underline{Z}$*/ dependent on the frequency f, measured with the arrangement of FIG. 21 (the measured value variation is entered as in FIG. 2).

FIG. 23 shows an arrangement for measuring the mechanical impedance of the carrier ring given single-sided clamping.

FIG. 24 shows the mechanical impedance/$\underline{Z}$/ of the carrier ring and of a six-ply PVDF transducer over the frequency f, measured with the arrangement of FIG. 23.

DESCRIPTION OF THE PREFERRED EMBODIMENTS

The sensory threshold for sinuisoidal deformations acting perpendicular to the skin surface is dependent on the stimulated area and on the body region, in addition to being dependent on other parameters. Fundamentally, the sensitivity increases with the area and in distal direction and reaches its maximum at the finger tips. In a preliminary test schematically shown in FIG. 1, therefore, the amplitude of a sinusoidal alternating voltage was identified dependent on the frequency which must be applied via lines 1.3 and 1.4 to the electrically conductive layers 1.1 and 1.2 lying on the large surfaces lying opposite one another in order to achieve the sensory threshold at a singly-ply PVDF winding of a band-shaped film 1. A 10 mm wide and 9 μm thick band 1 of PVDF was placed around the root of the index finger 2 of the ring hand and was fixed under slight mechanical tension. Five adult test subjects therewith identified their sensory threshold by means of oscillating tuning with a Bekesy Audiometer known, for example, from "Psychoakustik" (E. Zwicker).

Figure 2:
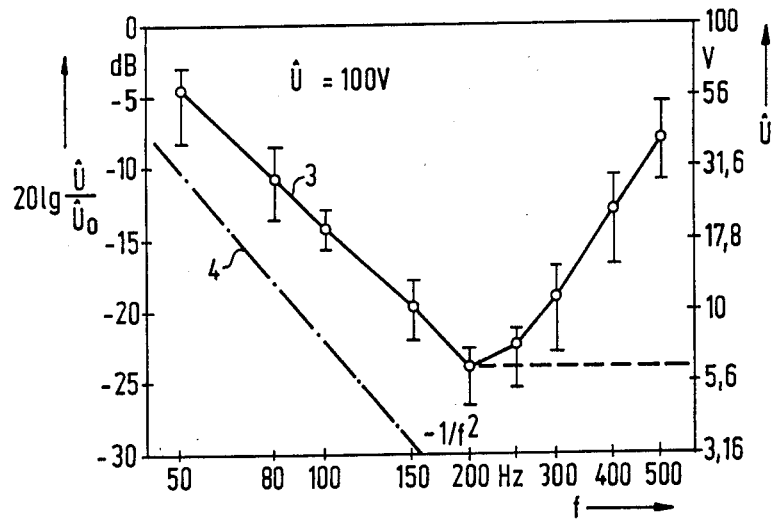
FIG. 2 shows the amplitude $\hat{U}$ of a sinusoidal alternating voltage at the threshold of sensation with the PVDF winding of FIG. 1 over the frequency f (the variation of the measuring breadth is respectfully entered at the measuring points by a vertical path).

FIG. 2 shows the central values and statistical fluctuations of the results. As indicated by the dot-dash straight line 4, the curve 3 initially falls with approximately 12 dB/Oct. It reaches a clear minimum at f=200 Hz and then rises sharply toward higher frequencies. The minimum voltage at f=200 Hz amounts to only $\hat{U}$=6.5 V. Deriving from the piezoelectric fundamental equations are:

$$D_3 = E_{33}{}^T \cdot E_3 + d_{31} \cdot T_1 \quad (1a)$$

$$S_1 = d_3 \cdot E_3 + S_{11}{}^E \cdot T_1 \quad (1b)$$

without influence of a mechanical stress $T_1$ (inverse piezo effect), $$S_1 = d_{31} \cdot E_3 \quad (2)$$

[deriving] from (1b), whereby $S_1$ is the dilatation of the film in longitudinal direction (the index "1" indicates the "machine direction"), $d_{31}$ is the piezoelectric constant and $E_3$ is the applied field strength in polarization direction (perpendicular to the film surface). For the calculation of the skin excursion x given f=200 Hz and $\hat{U}$=6.5 V, there follows from (2)

$$r = \frac{d_{31} U \, 1}{2 \, d} \quad (3)$$

whereby
  $\hat{x}$=r=radius change of the PVDF winding assumed to be circular.
  l=finger circumference (roughly 6 cm)
  d=thickness of the film (9 μm).
  With $d_{31}$=20.10$^{-12}$ m/V and $\hat{U}$=6.5 V, $\hat{x}$≈140 nm derives.

Figure 3:
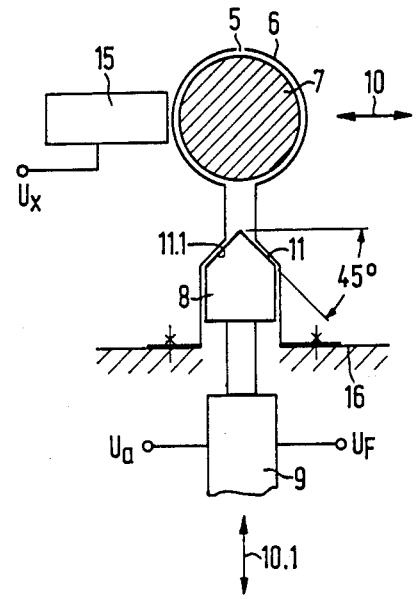
FIG. 3 shows an arrangement for measuring the threshold of sensation given non-limited, large-area skin stimulation at a finger joint.

An experimental arrangement schematically shown in FIG. 3 was employed for a comparable measurement of sensory threshold. Two 10 mm wide, semicircular spring steel parts 5 and 6 surround the finger 7. The sinuisoidal, vertical displacement indicated by double arrows 10 and 10.1 generated by an oscillatory stimulator 8 and impedance measuring head 9 is transformed via slanted planes (45°) 11 and 11.1 into horizontal motions of the half-rings 5 and 6. A skin deformation similar to that given the single PVDF winding (FIG. 1) is thereby achieved.

The sensory thresholds of six test subjects were identified with this arrangement by converting the acceleration value (measured signal $U_1$ of the impedance measuring head), set in the test by oscillatory tuning, by two-fold integration into the displacement x corresponding to the threshold. Correct operating of the motion transformation could be confirmed with an inductive path sensor 15 by means of non-contacting odometry (FIG. 3). The hand of the test subject was in contact with a bearing plate 16 only with the finger tips and the wrist; the test subjects were seated in a noise-proof and vibration-proof room and were deafened via headsets with white noice (L=85 dB) low-path limited at one kHz in order to prevent an acoustical detection of the mechanical stimulations.

Figure 4:
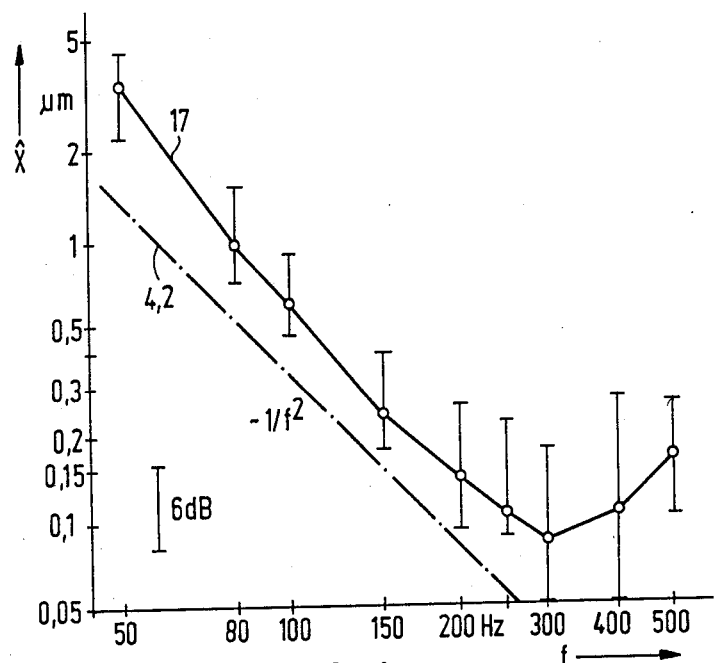
FIG. 4 shows the curve amplitude $\hat{x}$ at the threshold of sensation over the frequency f measured with the arrangement of FIG. 3 (with variation of the measured value as in FIG. 2).

The curve 17 of the sensory threshold curve in FIG. 4 and the dot-dash straightline 4.2, like curves 3 and 4 in FIG. 2, show an edge descending with 12 dB/Oct, show a minimum at slightly higher frequencies than in FIG. 2, and shown a noticeable rise for frequencies about 300 Hz. This curve of the sensory threshold is known and corresponds to the threshold curve of Paccini's mechano-receptor system which is independent of the point of stimulation given large stimulation areas.

The displacement $\hat{x}=130$ nm measured at f=200 Hz agrees well with the value $\hat{x} \approx 140$ nm calculated from equation (3) and thus confirms the validity of the film simulation with the mechanical model of FIG. 3.

The following statements can be derived from these determinations.

(a) piezoelectric polymers are fundamentally suitable as electro-mechanical transducers for tactile stimulators at the hand; when U=100 V is established as maximum voltage, a useable volume range $\Delta L=201$ g (100 V/6.5 V) dB=24 dB derives for PVDF given the best frequency f=200 Hz. At least this value can therefore be achieved for a voice signal processing.

(b) It derives from equations (2) and (3) that the thickness d of a film should assume optimally low values for a maximum longitudinal distortion $S_1$.

(c) The similarity of the threshold curves in FIGS. 2 and 4 indicates that mechanical resonances do not occur in the frequency range under consideration and short response times can therefore be counted on given a PVDF transducer.

Figure 1:
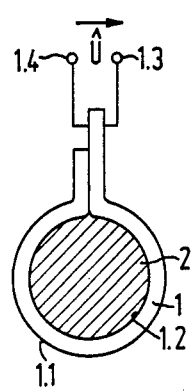
FIG. 1 shows an experimental arrangement for identifying the threshold of sensation voltage at a single-ply PVDF winding.

The PVDF winding forming a complete ring as in FIG. 1 is not particularly suitable as a transducer geometry when this stimulator to be worn by a hearing-impaired person is not removable, i.e. when it is not elastically withdrawable or unwindable. Moreover, the extremely thin metallization, i.e. the electrically conductive layers 1.1 and 1.2 of the film 1 which make up the winding are attacked by the acids contained in excretions of the skin, for instance perspiration.

The mechanical impedance of the load is increased when the film 1 is applied to a carrier ring for protection and for solidification. Greater forces would then have to be exerted in order to achieve a displacement x obtainable without a carrier. Employable a materials for the carrier ring are materials which are adequately stable given the required dimensions and which do not injuriously influence the film as well as its electrodes. The polyacetal plastic known under the name of Delrin, which is polyoxymethylene (POM) exhibits, for instance, such properties.

Figure 5:
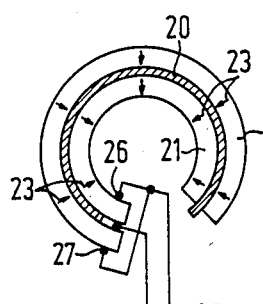
FIG. 5 shows a single-ply bimorph structure of a PVDF transducer with carrier ring constructed in accordance with the present invention.

A bimorph structure is possibly using PVDF, whereby the force achieved increases quadratically with the number of PVDF plies. FIG. 5 shows a bimorph structure wherein a respective ply 21 and 22 of PVDF is applied to the inside and outside of a carrier ring 20 which is three-fourths closed. Identically directed film polarization P, indicated with arrows 23, and the oppositely directed field strength of the signal voltage applied to the terminals 24 and 25 causes opposite distortion $S_1$ of the plies 21 and 22 of the film. When the outer ply 22 expands, the inner ply 21 contracts, whereby the desired deformation of the carrier ring 20 and, thus, of the skin surface is achieved. It can be seen from FIG. 5 that the bimorph structure must be symmetrical relative to the carrier ring; when both strips are applied to one side, the generated force compensate. This has been experimentally confirmed. The following reasons, however, oppose a bimorph structure:

(a) the uniform application of a plurality of PVDF plies 21 to the inside of the ring 20 is very technologically complex.

(b) The required, double contacting 26, 27 at the inside and the outside diminishes the operating reliability.

(c) When the inside connection is displaced onto the upper side of the ring by flipping the inside ply 21 over, the mechanical jeopardization of the film at the edge of the carrier ring 20 is considerably increased.

A bimorph structure is therefore not preferred.

FIGS. 6 through 9 show a transducer structure that can be simply applied and in turn removed from, for instance, a finger. A mechanical parallel connection of the individual plies 30 through 32 and, thus, an addition of the occurring forces is achieved by the multiple winding indicated in FIG. 6, i.e. a folded stack 1.6 on the upper side of the carrier ring 20.6. In comparison to the known layer systems, however, a contacting of the two electrically conductive outside faces of the tape is necessary (cf "J. Acoust. Soc. Im.", Vol. 70, No. 6, December 1981, 1605 and 1606). The dimensions of the transducer and the type of contacting may be seen from FIGS. 7 through 9.

The carrier ring 20.6 is 0.4 mm thick and 9 mm wide and is composed of POM. A sector 35 of 90° has been cut out therefrom in order to achieve an adequately firm mounting and a still adequately simple removability. Although a simple interruption of the ring girth is sufficient to obtain a resilient structure, the 90° cut-out achieves a spring effect, particularly for employment at fingers, which is especially beneficial for the removal and application of the transducer. By means of an appropriate selection of the inside radius (here, about 9 mm for a finger), an intimate mechanical contact to the skin surface is thereby also obtained. The cut edges of the film of which the plies 30 through 32 are composed and which are subject to shorts are mechanically protected by edges 36 and 37 (FIG. 8) of the carrier 20.6 which are 0.5 mm wide and drawn up 0.3 mm. Further, the winding 1.6 is protected at the outside with a layer 39 of silicone rubber.

In order to keep an increase in the impedance which is unavoidable due to glue layers for holding the plies 30 through 32 against one another as low as possible, the thickness of the glue layer should be small in comparison to the thickness of the film (d=9 μm). This is achieved by wiping the glue nearly completely off; thicknesses less than 0.3 μm can thus be achieved for the glue layers. A two-component glue on an epoxy resin basis has proven to be a suitable adhesive, enabling a rapid manufacture of multi-ply transducers as a result of its low potlife, and not attacking the metallization of aluminum applied as electrodes to the facing surfaces of the plies 30 through 32, and easily remaining permanently elastic.

The contacting of the electrically conductive layers 38 with which the band of PVDF from which the plies 30 through 32 are composed is coated is problematical because of the thin layers 38 serving as electrode and because of their unavoidable oxide layer, particularly given application of high fields. A contacting using a combination of thin copper foil 40 coated with conductive adhesive and high-quality two-component silver conductive glue 41 hardening at room temperature exhibited low resistance and great stability which was durable over a long time. The boundary condition of low processing temperatures in all steps of the manufacture is important since the Curie temperature of PVDF lies at 80° C. and de-polarization processes which lead to a reduction of the piezoconstants of PVDF begin above that temperature.

Figure 8:
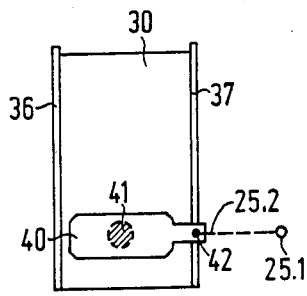
Figure 9:
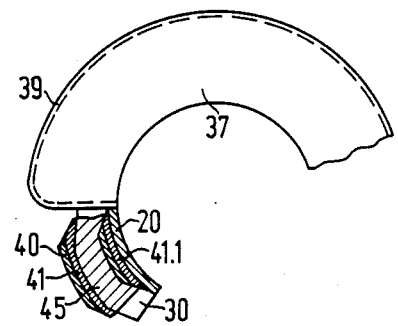

The selected contacting is shown in FIGS. 8 and 9. A rectangular piece (4 mm×7 mm) of the copper foil 40 and 40.1 is glued to one end of the carrier ring 20.6. Connection of the lead 25.2 from the connecting location 25.1 of this foil 40 is a solder location 42 at the edge of the ring. After the application of a slight quantity of silver conductive adhesive 41 in the center of the copper foil 40, the PVDF film 30 is glued on. Contacting of the upper side of the ply 30 of the stack occurs in the same way. The insulation of the two copper foils 40 and 40.1 from one another at the edge of the carrier ring 20.6 is achieved by introducing a thin mica sheet 45.

All further PVDF plies are already turned over before the contacting location in order to avoid a thickening at this point. It may be seen from FIG. 7 that the folding-back already ensues before reaching the connecting location. The overall thickness of the transducer thus remains under 1.2 mm up to fourteen plies of PVDF. This dimension is exclusively defined by the contacting location. A 9 μm thick film of bi-axially stretched PVDF film proved more suitable for this transducer structure than a film composed of a foil which is mono-axially stretched and which often exhibited cracks in the metallization at the sharp bends of the folds of the stack 1.6 (FIG. 7).

Figure 10:
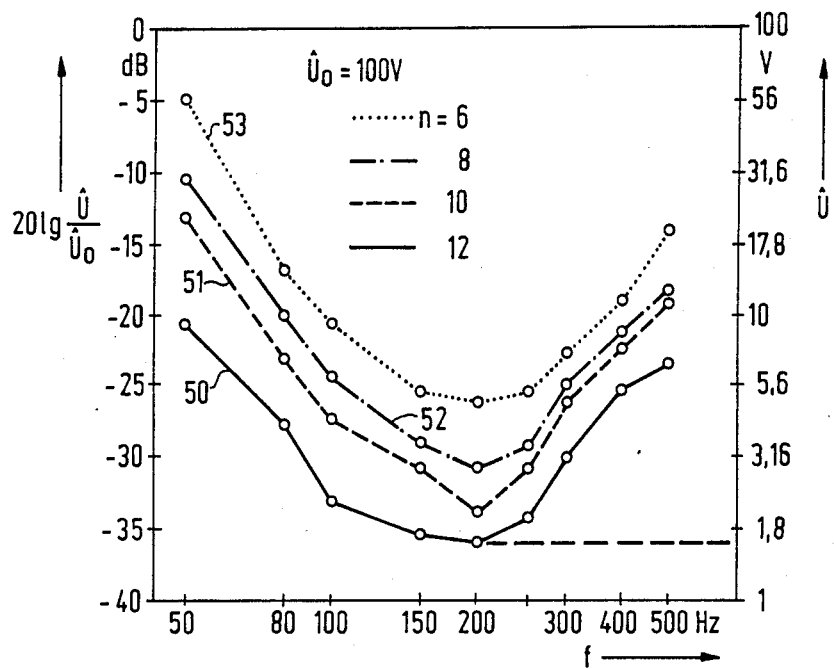
FIG. 10 shows the amplitude $\hat{U}$ of a sinusoidal alternating voltage at the threshold of sensation with multi-ply PVDF transducers dependent on the frequency and the number n of plys.
Figure 11:
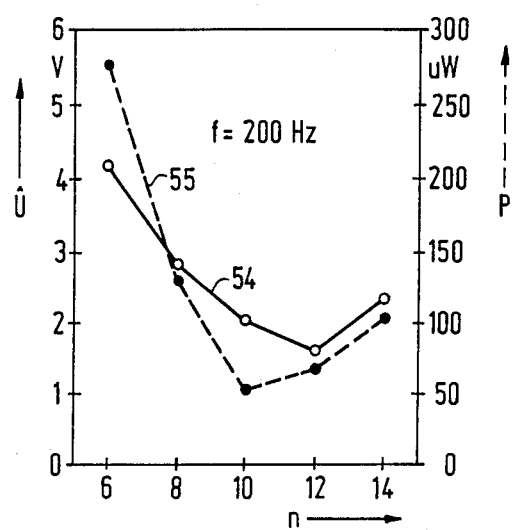
FIG. 11 shows the voltage amplitude $\hat{U}$ and consumed power P of multi-ply PVDF transducers at the threshold of sensation given f=200 Hz dependent on the number n of plies.

Sensory threshold measurements (cf. FIG. 2) were carried out with four test subjects with a transducer comprising this structure; the parameter was the number n of plies. The results are shown in the diagram of FIGS. 10 and 11. The central values are entered in the curves 50 through 55. The U-shaped threshold curve is preserved given variation of n=6 thourgh n=12, as are the slopes of the upper and lower edge. Given f=200 Hz, a lower threshold (Û≈5 V) already derives for n=6 than for the simple winding (FIGS. 1 and 2). Given an increasing number of plies, the voltage Û required for reaching the sensory threshold drops and, in the minimum given f=200 Hz and n=12, only amounts to Û$_{min}$≈1.6 V (FIG. 11). Given a greater n (n=14 is not shown in FIG. 10), Û$_{min}$ again increases; the consumed power already reaches its minimum given n=10 and amounts to P≈55 μW. P is slightly greater (≈70 μW) given n=12. The volume range, given n=12 and the best frequency f=200 Hz, reaches 36 dB (FIG. 10) when Û=100 V is established as the upper limit and is thus completely adequate for a voice signal processing wherein information is transmitted as a chronologically variable envelope of a sinuisoidal carrier oscillation (f$_T$=00 Hz). The transducer capacitance given n=12 amounts to C$_o$=37 nF. The overall weight lies below 2 g.

Figure 6:
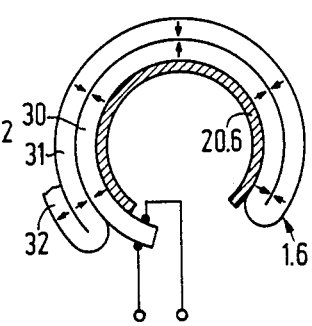
FIGS. 6 through 9 show the structure and means for skin contact of a multi-channel PVDF transducer constructed in accordance with the principles of the present invention without bimorph structure.
Figure 7:
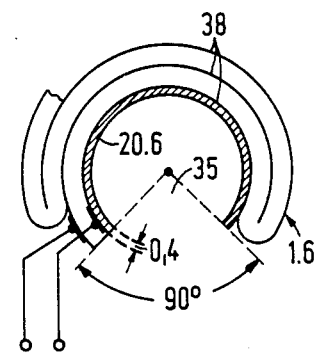

For the transmission of acoustic signals in the form of vibrations, an open ring shown in FIGS. 6 and 7 can be slipped onto the fingers 2.1 thorough 2.5 of a hand. It may be adequate to apply one transducer 46 to the root of the index finger 2.4, however, it can also be advantageous given using a multi-channel apparatus analogous to that described in French Pat. No. 12 31 085 to also apply transducers 46.1 through 46.4 to the other fingers.

Thus, a signal divided into various channels of different frequency can be transmitted in correspondingly characteristic division onto the individual fingers in order to improve comprehension.

As shown in FIG. 13, a folded stack 47 can also be obtained from a PVDF film which has the shape of a rectangular foil whose one side is as long as the circumference of the ring arc to be bent from the stack 47 and which is folded parallel to this side at intervals corresponding to the width of the stack. A folded stack 47 is thus obtained whose folding lies at right angle to that of FIGS. 6 and 7. In electrical terms, there is complete agreement with the stack 1.6. This is especially indicated in FIG. 13 by the identification of the layers 30.1, 31.1 and 32.1 which are to come to lie above one another in the stack. The electrically conductive coatings 38.1 and 38.2 then lie at the outsides of these layers. After the fold shown in FIG. 13 has been telescoped in accord with the arrows 39.1 and 39.2, a folded stack 1.7 indicated in FIG. 14 is obtained. In accord with the embodiments of FIGS. 6-9, this can be applied to a carrier ring in accord with 20.6 and can be contacted as shown in FIG. 8.

The large volume range remains chronologically stable when no depolarization processes arise due to the field strengths (E>100 KV/cm) occurring given Û=100 V. The long-term stability of d$_{31}$ was therefore tested in a long-duration test. A suitable method is schematically shown in FIG. 15. A 10 mm wide strip 60 of PVDF was clamped at both sides in mounts 61 and 62 under slight mechanical stress. A thin gap 63 of the metallization 64 was etched free in the center at one side of the surface, whereas that on the opposite side remained continuous. The film halves which arose in this fashion were contacted at the edge at locations 65, 66 and 67, 68. Deriving from the mechanical coupling of the halves, the boundary conditions from (1) and the equations (1a) and (1b) is $$d_{31} = \sqrt{\frac{2\, U_2 \cdot E^T}{U_1 \cdot c^E}} \quad \text{for } U_1/U_2 > 1$$

with $$E^T = E_r \cdot E_o = 9.7 \cdot 10^{-11} \frac{F}{m} \quad \text{(Dielectric constant)}$$

$$E = 2 \cdot 10^9 \frac{N}{m^2} \quad \text{(Modulus of elasticity)}$$

Figure 17:
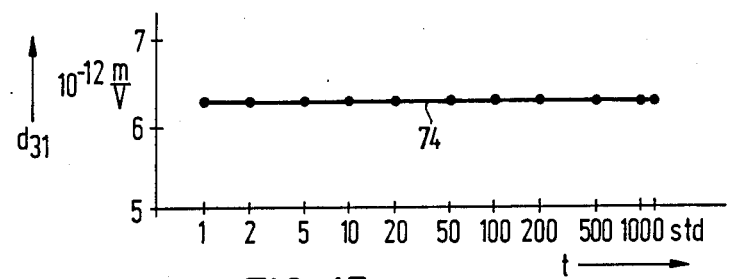
FIG. 17 shows the long-term stability of the constant $D_{31}$ given f=200 Hz and $\hat{U}_1$=160 V which is obtainable in accord with FIG. 15.

The progression measured with this arrangement is shown in a diagram in FIG. 16 by the curve 73 of the constant d$_{31}$ over the frequency given Û$_1$=20 V. Given f=1 kHz, d$_{31}$=6.5·10$^{-12}$ V/m) applies and agrees well with the maker's specification (d$_{31}$=7 to 8·10$^{-12}$ V/m). The constant d$_{31}$ decreases slightly toward low frequencies, but can be assumed as constant in the range of interest 50 Hz<f<500 Hz. The long-term stability was investigated with a sinuisoidal (f=200 Hz) and alternating field having no dc component having the strength E$_3$=180 KV/cm (Û=160 V). This field strength roughly corresponds to 10% of the polarizing field strength of the PVDF film. A change of the constant d$_{31}$ did not occur within a time span of 1200 hours, as proceeds from the horizontal course of the line 74 in FIG. 17. The transducer dynamics can therefore be assumed to be time-invariant, even when voltages far above U=100 V are applied at mean frequencies.

For checking the loadability of the described contacting, the left film half of the arrangement in FIG. 15 was subjected to low-pass-limited white noise in Gaussian pulsed mode ($t_{on}$=500 ms, $t_{off}$=560 ms, rise-fall time constant of the envelope=1 ms) given f=8 kHz. The field strength amounted to $E_3$=120 kV/cm; the current $J_1$ (FIG. 12), at roughly 6 mA, was greater by the factor 3 than the value that is achieved in a twelve-ply transducer give f=200 Hz and $E_3$=100 kV/cm (Û=100 V). After a test duration of 1000 hours, no modification in any parameter could be measured. The contact resistance $R_K$ of the contacting lay at $R_K \leq 3/0$ hm in all specimens; stray power $P_K$ thereby arising in the contacting amounts to $P_K$=12 μW given J=2 mA and is negligible in comparison to the total power consumption $P_{Tot}$ of a 12-ply transducer ($P_K$=4·10$^5$·$P_{tot}$) given Û=100 V and f=200 Hz.

In a further test series, matching of the twelve-ply transducer to the medium of the skin surface was tested. Little concerning the identification of the mechanical skin impedance $Z_H^*$ required for such a test is known from the literature. In general, $Z_H^*$ is dependent on the measuring location, the bearing pressure, the stimulated surface and the type of surface limitation. A dispersion of the phase velocity is also known to occur. When $c_H \approx 5$ m/s at f=200 Hz is established for the propagation speed in the skin surface and the density is established at $\rho_H \approx 10^3$ kg/m$^3$, then $$Z_H = \rho_H \cdot c_H \approx 5 \cdot 10^3 \frac{Ns}{m^3}$$

derives for the intrinsic impedance $Z_H$.
For PVDF, $$Z_{PVDF} = 3.9 \times 10^6 \frac{Ns}{m^3}.$$

Following therefrom is a reflection factor $$r = \frac{Z_{PVDF} - Z_H}{Z_{PVDF} = Z_H} \approx 0.997$$

for the single-ply PVDF winding of FIG. 11. This high reflection factor (r≈1) suggests a very low efficiency of the transducer (for comparison: r=0.44 given transition in water).

Figure 18:
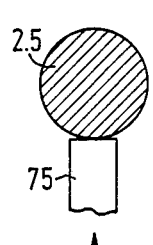
FIG. 18 schematically shows an arrangement for measuring the mechanical skin impedance without limitation given small stimulation areas ($S_S$=0.28 cm$^2$).
Figure 20:
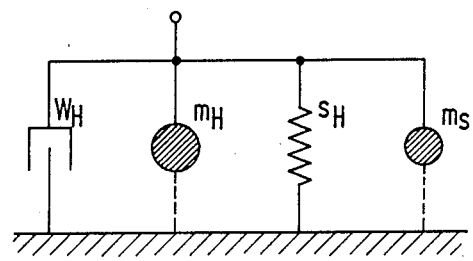
FIG. 20 shows a mechanical equivalent circuit diagram of the impedance/$\underline{Z}$*/ shown in FIG. 19.
Figure 19:
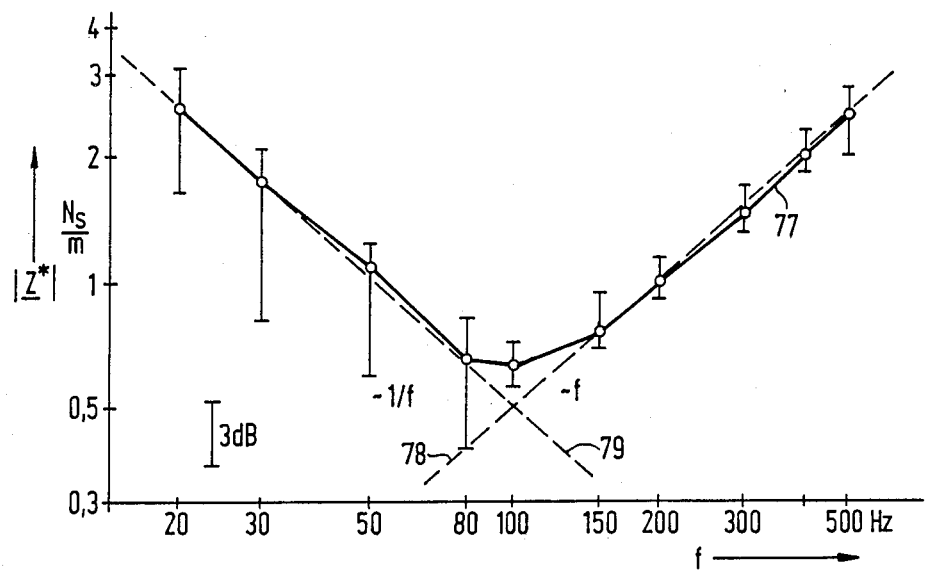
FIG. 19 shows the mechanical impedance/$\underline{Z}$*/ dependent on the frequency f, measured with the arrangement of FIG. 18 (with measured value variation as entered in FIG. 2).

The measured results of a mechanical impedance $Z^*$/ given small die surfaces ($S_s$=0.28 cm$^2$) without external limitation of the skin surface (schematically shown in FIG. 18) are shown in FIG. 19 in a diagram including the curve 77. The point of stimulation was the underside of the index finger root 2.5 of the right hand to which a die 75 is applied. Central values and probable variation ranges which were defined by six test subjects are entered in FIG. 19. In the range from 20 Hz through 80 Hz, /Z*/ drops with 6 dB/Oct, reaches a clear minimum at f=100 Hz and increases with 6 dB/Oct toward higher frequencies (the exact slopes ~1/f or ~f are entered with the dashed lines 78 and 79). A mechanical parallel resonant circuit with the elements skin friction drag $W_H$, skin mass $m_H$ and skin stiffness $S_H$ exactly describes this frequency response (FIG. 20). The die mass $m_s$ must also be considered as a parallel element. The expression in complex notation for the circuit in FIG. 20 is $$Z^* = W_H + jw\, m_H = \frac{s_H}{jw} + j \cdot w \cdot m_s$$

From this equation and from FIG. 19, the individual elements can be calculated at $$W_H = 0.65 \frac{Ns}{m}$$

$$m_H = 0.37\, 10^{-3} \text{kg}$$

$$s_H = 330 \frac{N}{m}.$$

Given circular areal limitation ($S_H$=0.64 cm$^2$), comparative measurements at the inside of the underarm yielded:

$$W_H = 0.2 \frac{Ns}{m}$$

$$m_H = 0.25 \cdot 10^{-3} \text{ kg}$$

$$s_H = 200 \text{ N/m}.$$

In this case, too, the mechanical skin impedance can be approximated very well to the local limitation of a skin area ($S_H$<1 cm$^2$) by means of a damped mechanical parallel resonant circuit.

Figure 21:
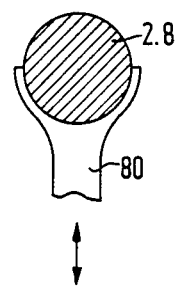
FIG. 21 schematically shows an arrangement for measuring the mechanical skin impedance without limitation given large stimulation areas ($S_S$=2.8 cm$^2$).

In order to simulate the large-area, non-surface-limited stimulation by the PVDF transducers, a semi-annular, rigid geometry of a die 80 was selected (FIG. 21, $S_s$=2.8 cm$^2$). The mechanical skin impedance /$Z_H^*$/ exhibits the curve referenced 85 in FIG. 2 after elimination of the die mass $m_s$. The measuring location was again the underside of the index finger root 2.8 of the right hand. The impedance /$Z_H^*$/ is approximately constant for frequencies under 200 Hz and amounts to /$Z_H^*$/≈4 Ns/m; above f=200 Hz; /$Z_H^*$/ drops with 6 dB/Oct in accord with a stiffness $s_H$=5400 N/m. The frequency-independent curve of f≦200 Hz corresponds to a friction drag $W_H$4 Ns/m. Given large-area stimulation (S>2.5 cm$^2$), thus, the mechanical skin impedance noticeably differs from the impedance measured given surface limitation or small stimulation areas (S<0.5 cm$^2$). The frequency response of /$Z_H^*$/ in FIG. 2 indicates a greatly damped, mechanical series resonant circuit. Given measurements at the thigh ($S_H$=5.3 cm$^2$, not area-limited), values of 1 ... 4 Ns/m are obtained for /$Z_H^*$/ in the range of 100 Hz ... 300 Hz; these amounts agree well with our own measurements (FIG. 22). However, a closed analytic expression for /$Z_H^*$/ cannot be derived therefrom.

The mechanical impedance of the carrier ring 20.9 given single-sided clamping at the die 90 of FIG. 23 is shown in a diagram in FIG. 24 (solid curve 95). The same mechanical equivalent circuit diagram (FIG. 20) can be derived from the frequency response as in small-area skin stimulation; the elements of effective ring mass $m_R$, effective stiffness $s_R$ and of friction drag $W_R$ are calculated at $$m_R = 0.11 \cdot 10^{-3} \text{kg}$$

$$s_R = 620 \frac{N}{m}$$

-continued $$W_R = 0.23 \frac{Ns}{m},$$

and lie on the same order of magnitude as the elements of the mechanical skin impedance given small-area or area-limited stimulation. After application of six plies of PVDF on the carrier ring, the element values are increased to (dotted curve 96 in FIG. 24)

$$m'_R = 0.18 \cdot 10^{-3} kg$$

$$s'_R = 2200 \frac{N}{m}$$

$$W'_R = 0.37 \frac{Ns}{m}.$$

The increase in stiffness in most noticeable; the resonant frequency shifts from $f_o=230$ Hz to $f_o=330$ Hz. When these data are extrapolated to a twelve-ply transducer, the amounts of the mechanical impedances of the transducer ring and of the skin surface lie on the same order of magnitude (cf. FIG. 22).

When the impedance $/\underline{Z}_H*/\simeq 4$ Ns/m for large-area skin stimulation is used as the basis for f=200 Hz, $$\mu = \frac{P_{mech}}{P_{el}} = 4.8 \cdot 10^{-4} \simeq 0.5\% \text{ o}$$

derives for the transducer efficiency $\mu$ of the single-foil winding of FIG. 1, with $$P_{mech} = \bar{x}^2 \cdot 4 \cdot 2 \cdot f^2 / \underline{Z}*_H /$$

whereby $\bar{x}$=effective displacement value at the sensory threshold. Under the same boundary conditions, $$\mu = 3.8 \; 10^{-4} \simeq 0.04\%$$

is obtained for the efficiency of the twelve-ply PVDF transducer. Following from the slight difference between $\mu$ and $\mu'$ is that the low efficiency (as excepted) is principally attributed to the large intrinsic impedance discontinuity in the transition from PVDF to the skin surface, and the carrier ring does not represent any additional mismatching; this is confirmed by the estimate of the mechanical impedance level.

Figure 25:
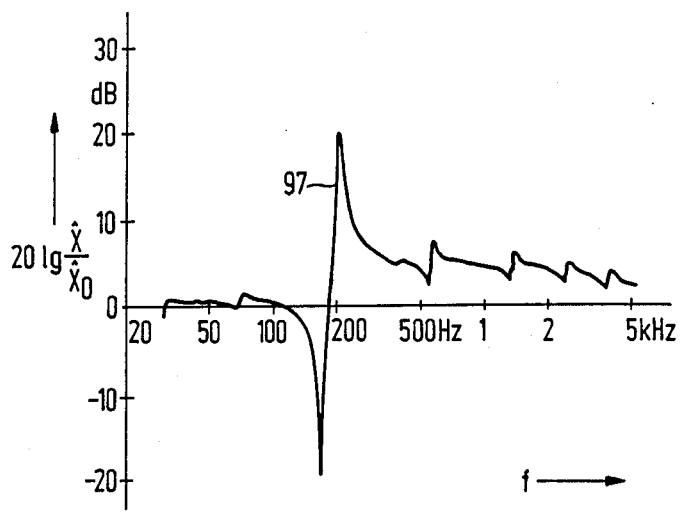
FIG. 25 shows the no-load curve $\hat{X}$ of a twelve-ply PVDF transducer without clamping over the frequency f (reference value $\hat{x}_o$ arbitrary).

The displacement in no-load and under skin load was qualitatively measured at the twelve-ply PVDF transducer; the measuring sensor was a ply of PVDF foil glued to the inside of the carrier ring with which the distortion $S_1$ and thus the excursion component perpendicular to the skin surface was measured. The frequency response of the displacement in no-load is shown with the curve 97 in a diagram in FIG. 25. The displacement remains nearly constant in the frequency range under consideration; the mechanical resonant frequency now lies at $f_o=209$ Hz. The additional resonance at f=170 Hz is to be attributed to the mechanical impedance of the connecting lines. The decrease of $f_o$ from over 300 Hz to about 200 Hz is explained by the great decrease of the effective stiffness given free oscillation of the transducer (cf. FIG. 24).

Figure 26:
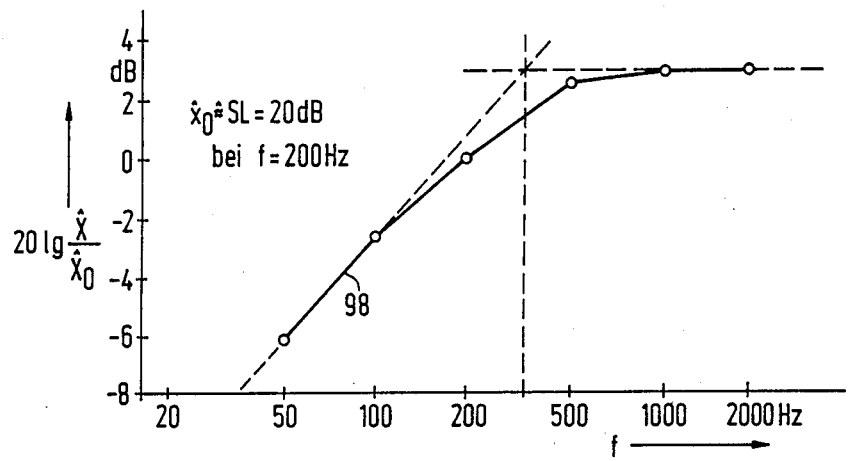
FIG. 26 shows the curve $\hat{X}$ of the transducer of FIG. 19 under skin load (index finger root of the right hand) over the frequency f; the central values of four test subjects are shown, reference value $\hat{X}_o$.

The frequency response of the displacement x under skin load is shown with the curve 98 in a diagram in FIG. 26 (central values of four test subjects). Since an absolute measurement was not possible, the measuring points were normed to the value $x_o$ at f=200 Hz. As in no-load (cf FIG. 25), the measurement ensued given impression of voltage onto the terminal posts of the transducer. The voltage was selected such that an displacement level over the threshold SL of 20 dB occurred given f=200 Hz.

The displacement rises with approximately 3 dB/Oct up to f=300 Hz, remains constant toward higher frequencies and achieves a value in this region which is only 12 dB lower than in no-load. A resonance step-up is not measurable under load. When, as in FIG. 2, the mechanical skin impedance for frequencies above 300 Hz is set at $$/Z_H* (f > 300 Hz)/ = \frac{\hat{F}}{\hat{v}} = \frac{\hat{F}}{\hat{\dot{x}}} = s$$

with $\hat{F}$: force amplitude, $\hat{v}$: velocity amplitude, it follows that the displacement x must be frequency-independent in this range. This is confirmed by the values of a measurement entered in a curve 98 (FIG. 26). The decrease of the displacement from 300 Hz toward lower frequencies cannot be explained by a simple formulation of the mechanical skin impedance. A complete mechanical equivalent circuit diagram of the skin impedance has therefore been foregone. Non-linearities of the skin impedance could not be measured up to a level of 40 dB above the threshold; accordingly, a spectral analysis of the measuring foil signal yielded harmonic distortion attenuations greater than 55 dB under skin load up to transducer input voltages $\hat{U}=150$ V in the range 50 Hz<f<1000 Hz.

Figure 27:
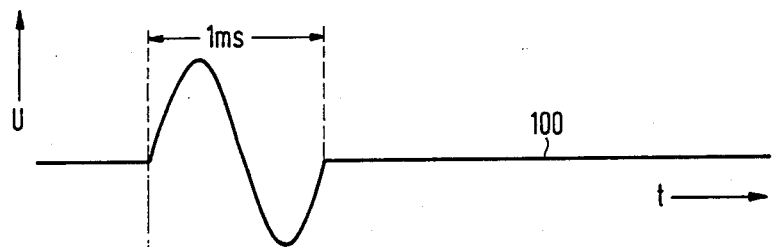
FIG. 27 shows the electrical input signal $\hat{U}$ at a twelve-ply PVDF transducer ($\hat{U}$=20 V).
Figure 28:
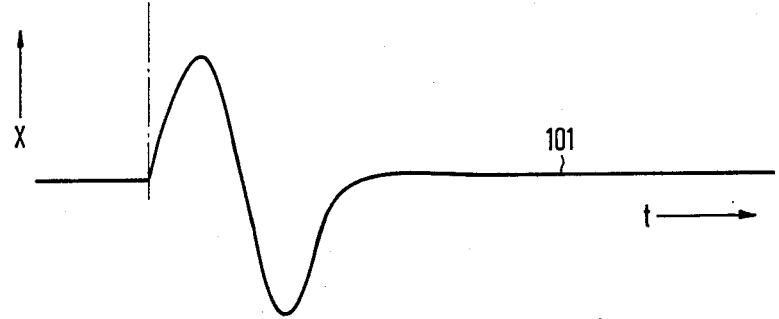
FIG. 28 shows the curve of the transducer under skin load (qualitative measurement).

As a consequence of the extremely low intrinsic mass of the transducer and the attenuation due to the skin impedance, the response time of the system under skin load is negligible in comparison to the time constants which are prescribed by the central-nervous processing mechanisms of the sense of touch. FIG. 27 shows the displacement x of a twelve-ply transducer under skin load measured with a measuring foil ply with the curve 100 in FIG. 24. When a sinuisoidal voltage pulse with U=20 V is applied to the transducer, the curve 101 in accord with FIG. 28 derives. The voltage curve is converted directly into a deformation of the ring and, thus, of the skin surface. Pulse repetition frequency modulations, for example for the transmission of the corresponding coded fundamental voice frequency, can therefore be accurately achieved with this type of stimulator.

Although modifications and changes may be suggested by those skilled in the art it is the intention of the inventors to embody within the patent warranted hereon all changes and modifications as reasonably and properly come within the scope of their contribution to the art.

We claim as our invention:

1. A device for converting electrical signals into signals tactilely perceivable by a human by contact with a portion of the body comprising:
   an electro-mechanical transducer having a vibratory member consisting of at least one ply of a film of polyvinylidene fluoride piezoelectric material in direct contact with said body portion;
   a carrier for said film, said carrier and said film forming an interrupted ring; and
   electrically conductive coatings on both sides of said film adapted for applying said electrical signals therebetween.

2. A device as claimed in claim 1, wherein the interruption in said ring is a gap of at least about 90°.

3. A device as claimed in claim 1, wherein said ring is sized for fitting around a human finger.

4. A device as claimed in claim 3, wherein said ring is formed by a folded stack of said film carrier and said with said coatings thereon, and wherein electrically conductive coatings having the same polarization disposed at the outside surfaces of the ring are adjacent each other.

5. A device as claimed in claim 4, wherein the interruption in said ring is a gap formed by folding said film with said coatings thereon back over and outside of said ring.

6. A device as claimed in claim 4, wherein said film is a rectangular film having one side corresponding to the circumference of said ring and which is folded parallel to said one side at intervals corresponding to said length.

7. A device as claimed in claim 3 further comprising a plurality of said transducers forming respective rings.

8. A device as claimed in claim 7, wherein one said ring is provided for each finger and the thumb of one hand.

9. A device as claimed in claim 1, wherein said carrier consists of polyoxymethylene.

10. A device as claimed in claim 1, wherein said carrier has spaced side walls forming a channel receiving said film, said carrier and said walls having a width and a thickness corresponding to the width and thickness of said film.

11. A device as claimed in claim 10, wherein said carrier has a thickness of about 0.4 mm and a width of about 9 mm.

12. A device as claimed in claim 10, wherein said carrier is bent into a ring having a diameter of approximately 9 mm.

13. A device as claimed in claim 12, wherein said electrically conductive coating on both sides of said film is aluminum and wherein said film is folded into a plurality of plies to form a stack, and wherein said walls of said carrier correspond to the thickness of said stack.

14. A device as claimed in claim 13, wherein said stack is 9 mm thick.

15. A device as claimed in claim 13, wherein the number of plies in said stack is in the range of 6 through 14.

16. A device as claimed in claim 15, wherein the number of plies in said stack is 12.

17. A device as claimed in claim 1, further comprising a protective coating covering said film with said electrical coating.

18. A device as claimed in claim 17, wherein said protective coating consists of silicone rubber.

19. A device as claimed in claim 1, further comprising a copper foil glued to each of said electrically conductive coatings with conductive adhesive for making a contact for the respective coatings.

20. A device as claimed in claim 19, wherein said copper foil projects laterally beyond said film.

21. A device as claimed in claim 20 further comprising a mica sheet disposed between the projecting portions of said copper foil.

22. A device as claimed in claim 1, wherein said film is in the form of a stack having a plurality of overlying plies, said plies being glued together with an adhesive.

23. A device as claimed in claim 22, wherein said adhesive is a two-component epoxy adhesive.

* * * * *